AEROSOL DISPENSING PACKAGE

Original Filed May 7, 1962 2 Sheets-Sheet 1

INVENTOR.
Philip Meshberg
BY
Johnson and Kline
ATTORNEYS

AEROSOL DISPENSING PACKAGE

Original Filed May 7, 1962 2 Sheets-Sheet 2

INVENTOR.
Philip Meshberg
BY
Johnson and Kline
ATTORNEYS

United States Patent Office

Re. 26,304
Reissued Nov. 21, 1967

26,304
AEROSOL DISPENSING PACKAGE

Philip Meshberg, 15 Stoneleigh Road,
Fairfield, Conn. 06430

Original No. 3,184,115, dated May 18, 1965, Ser. No. 192,737, May 7, 1962. Application for reissue Aug. 11, 1965, Ser. No. 479,365
25 Claims. (Cl. 222—156)

Matter enclosed in heavy brackets [ ] appears in the original patent but forms no part of this reissue specification; matter printed in italics indicates the additions made by reissue.

The present invention relates to an aerosol package and more particularly to an aerosol package having an uncovered glass bottle disposed in a protective housing and to dispensing means therefor.

Heretofore, in packaging aerosol under pressure in a glass container, it has been the practice to provide a plastic coating on the bottle to prevent the glass fragments of the bottle from causing injury should the bottle break because of excess pressure therein or for other reasons. While the plastic coating served this purpose, it did not prevent the material under pressure in the bottle from projecting the valve stem carried by the top of the bottle at a high rate of speed, with the danger of injury or damage.

The present invention overcomes these difficulties by providing a plain glass bottle having the valve secured by a mounting means to the neck of the bottle with the valve stem projecting therefrom. The bottle is then disposed within a protective housing, preferably of molded shock resistant plastic, having a bottom and side walls and having a closure therefor which is adapted to be secured to the walls of the housing and have a portion extending over the end of the bottle to prevent the valve from being projected in the event of breakage of the bottle.

The protective housing is provided with venting means to permit the pressure to be dissipated, in the event of breakage of the bottle, without damaging the housing. Preferably, part of the venting means can be formed as apertures adjacent the bottom of the housing which serves as sight openings to permit the user to determine when the enclosed container is empty.

The basic unit can be provided with various types of dispensing means to form the dispensing package. In one form of the invention the dispensing means includes telescoping sleeves forming a directing chamber for directing the material for oral application, the telescopic sleeves having means for preventing inadvertent operation of the device when in a retracted inoperative position.

In another form of the invention a fluid directing sleeve is pivotally mounted on a projection of the closure for the housing and cooperates with the housing to be moved into a dispensing position.

In other forms of the invention the dispensing means is provided with an elongate dispensing passage which places the nozzle at the back of the applying chamber to provide for a better distribution of the spray formed by the nozzle.

While the closure for the walls of the housing can be heat sealed in position so as to form a unitary structure, in the preferred form of the invention the interlock between the closure and the walls of the protective housing is formed by lancing out or otherwise forming tongues in the side walls which will cooperate with the closure member to prevent it from being moved out of closing relation. In some instances the lanced out tongues cooperate with a shoulder on the closure member to permit sliding movement of the closure for dispensing the material.

Other features and advantages of the invention will be apparent from the specification and claims when considered in connection with the accompanying drawings in which:

Figure 1:
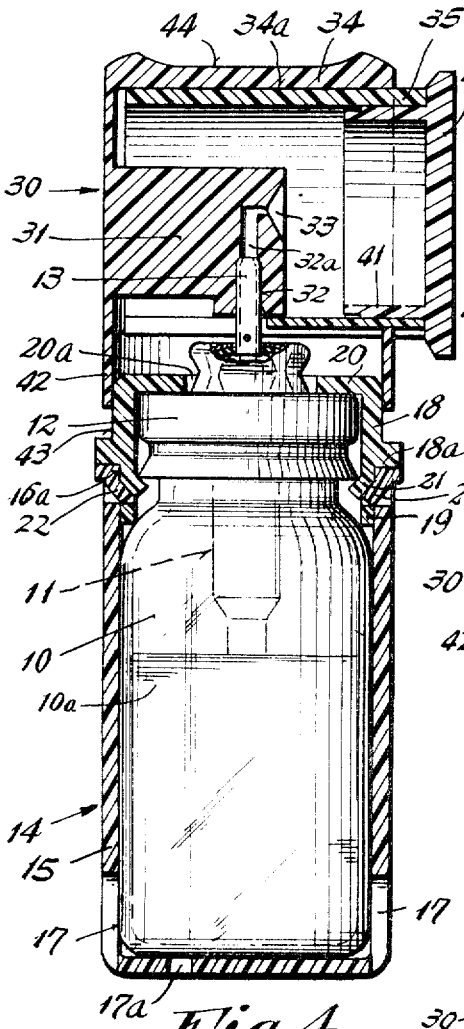
FIGURE 1 shows a longitudinal sectional view of one form of the dispensing package with the dispensing sleeve in retracted position.
Figure 2:
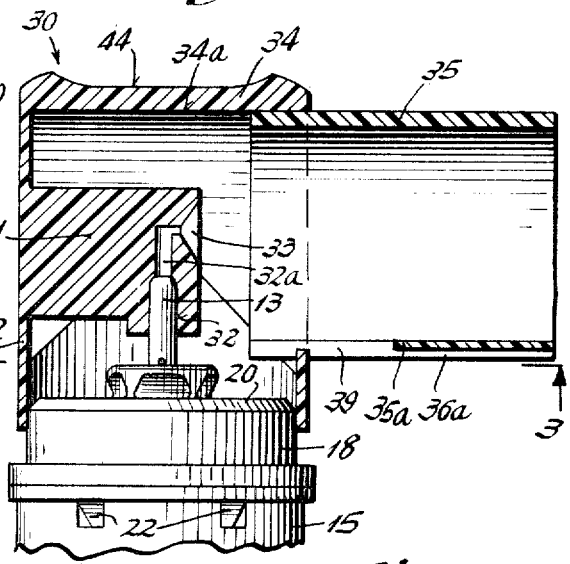
FIG. 2 is a view similar to FIG. 1 with the sleeve in projected operative position.
Figure 3:
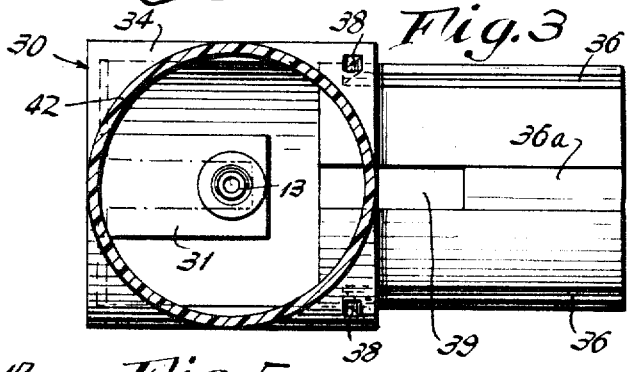
FIG. 3 is a sectional view taken along lines 3—3 of FIG. 2.
Figure 4:
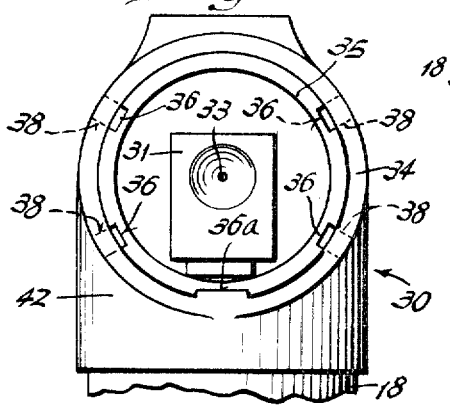
FIG. 4 is a front view of a dispenser as shown in FIG. 2.

As shown in the drawings, the basic unit or container includes a breakable bottle 10, which may be uncoated the housing is formed from a strong shock resistant material 10*a* under pressure. This can be any sort of aerosol material having a propellent to provide a pressure for dispensing the material from the bottle under control of a valve 11 which may be a metering or nonmetering valve, as required, and which is secured in place by the valve mounting ferrule 12 and has a valve stem 13 provided with the usual passages projecting therefrom.

The bottle is positioned in a plastic protective housing 14 having side walls 15 and a bottom wall 16. Preferably, the housing is formed from a strong shock resistant material, such as polyethylene or the like, which will absorb shock to resist breakage of the bottle by outside forces as when the device is dropped or hit a blow and which is strong enough to resist expansive forces such as might be present if the bottle should break because of excess pressure therein. It is provided with vents 17, 17*a*, which are very small so as to prevent passage of glass fragments therethrough, for permitting passage of gaseous material from the housing to relieve the pressure therein in the event the bottle should break.

Figure 5:
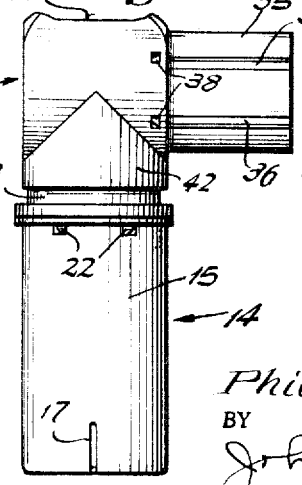
FIG. 5 is a side view of the dispenser.
Figure 6:
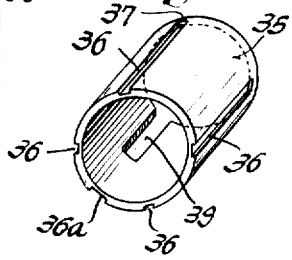
FIG. 6 is a perspective view of the telescopic sleeve.

In the preferred form of the invention the vents 17 are positioned on opposite sides of the housing and are formed as elongate slits, as shown in FIGS. 1 and 5, which also provide sight openings so that the contents of the bottle can be viewed and the user determine when the bottle is empty or almost empty.

While sliding shutters or the like may be provided to close the sight opening in the case of materials in the bottle which may be affected by light passing through the slits, in the herein illustrated form of the invention plain unshuttered slits are employed.

The bottle is inserted through the open end 16*a* of the housing and the housing is closed by a closure 18. The closure has a socket or shoulder 18*a* thereon engaging the end of the side walls 15 to limit insertion of a depending flange 19 thereon adapted to extend into the end of the housing. The closure also has an end wall 20 extending over the mounting ferrule of the valve and provided with an opening 20*a* through which the stem of the valve passes to project above the container.

The closure may be heat sealed in place or, as herein illustrated, side wall 15 and flange 19 are lanced to provide inwardly and downwardly extending interlocked tongues 21, 22 as shown in FIG. 1, at a plurality of places around the side wall to effectively lock the closure to the container and prevent the closure from moving out of closing position under pressure should the bottle break. Further, if desired, the ends of the flange 19 can cooperate with the bottle as shown in FIG. 1 to provide a means for centering and holding the bottle in proper position within the housing.

Since the end wall 20 overlies the valve mounting ferrule, it will prevent the valve from being projected out of the container in the event that it is released due to the breakage of the bottle.

This basic container unit including the bottle and housing may be used with various types of dispensing means. As herein illustrated, the dispensing means will be described as various forms of applicators for use in directing the aerosol into body cavities.

In the form of the invention shown in FIGS. 1–6, the dispensing means or button 30 has a central portion 31 provided with a bore 32 for receiving the end of the valve stem to be secured thereto for movement therewith. A passage 32*a* extends from the stem and opens in a nozzle 33. While a mechanical break up or the like may be used, the nozzle herein illustrated is a conical depression in the button for dispersing the fluid as it passes therefrom.

The dispensing means has an outer wall 34 formed by a transverse bore 34*a* closed at one end, said bore having slidably mounted therein a tubular sleeve 35 to form a directing chamber concentric with the nozzle.

In the illustrated form of the invention the transverse bore and sleeve are cylindrical and means are provided for controlling the sliding movement of the sleeve with respect to the bore. This is accomplished by providing longitudinal external grooves 36 in the sleeve terminating short of the inner end of the sleeve to form an abutment 37 and by providing lanced out tongues 38 in the outer wall extending into the grooves to prevent rotation of the sleeve in the bore while permitting sliding movement therein with the abutments 37 engaging the ends of the tongues to limit the outward movement of the sleeve.

The sleeve has a slot 39 in the bottom thereof in line with a groove 36*a* which permits the sleeve to straddle the valve stem and to move the blocking portion 35*a* under the central portion 31 to prevent it from moving inwardly to a position in which it would operate the valve when the sleeve is in its retracted inoperative position, as shown in FIG. 1.

The directing chamber can be closed by a plug or closure member 40 having a sleeve-like flange 41 adapted to be inserted in the open end of the sleeve 35.

In order to prevent foreign material from passing into the container through the opening 20*a*, the dispensing device is provided with a depending skirt 42 which closely embraces the sides 43 of the closure to provide a complete enclosure therefor while still permitting the dispensing button to be moved downwardly toward the container by finger pressure being applied to a top flat surface 44 of the dispensing means when it is desired to actuate the valve through the operation of the valve stem to dispense material therefrom.

Figure 7:
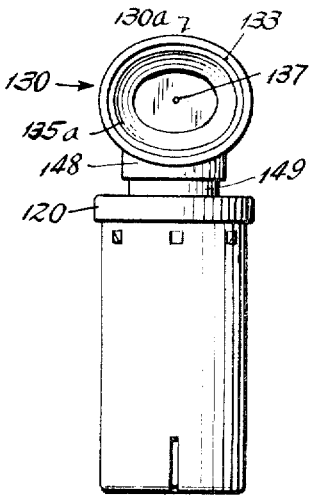
FIGS. 7 and 8 show a front view and a longitudinal sectional view of another form of package.
Figure 8:
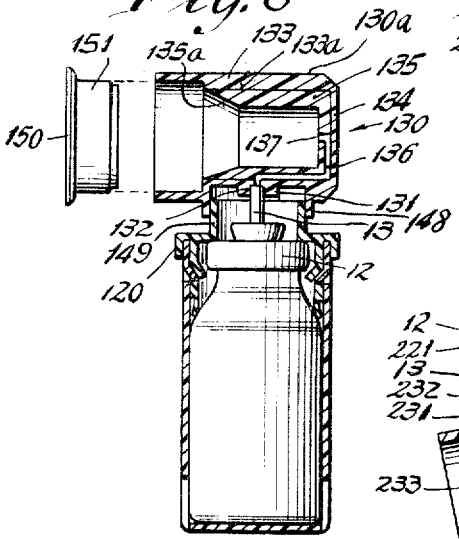

In the form of the invention shown in FIGS. 7 and 8 the basic unit as described above is provided with a dispensing device which is oval in cross section and may be used as an oral applicator or as an "eye cup," depending upon the material in the container.

The dispensing means 130 as shown in FIGS. 7 and 8 includes a central portion 131 having a bore 132 to receive and be mounted on the end of the valve stem 13 and has a wall 133 formed by a transverse bore 133*a* which is provided with a closed end 134. A thimble 135 is inserted in the transverse bore 133 and is provided with an elongate groove 136 opening in the bottom of the thimble adjacent the closed wall of the bore of the dispensing device to provide a nozzle 137 for dispensing the material from the container with a predetermined spray pattern. This locates the nozzle a predetermined distance from the open end of the bore and preferably in a position concentric with the bore which forms the dispensing chamber for the device. Preferably, the open end of the thimble is beveled at 135*a* so as not to interfere with the spray pattern established by the nozzle.

A depending skirt 148 extends from the dispensing means and slides over the wall 149 of the closure 120 to provide for sliding movement of the dispensing means as it moves the stem inwardly under finger pressure applied to the top portion 130*a* to control the valve to dispense the material from the bottle.

If desired, a closure plug 150 having a flange 151 insertable in the open end of the bore 133*a* in the dispensing means may be provided for closing the bore when the device is not in use.

Figure 9:
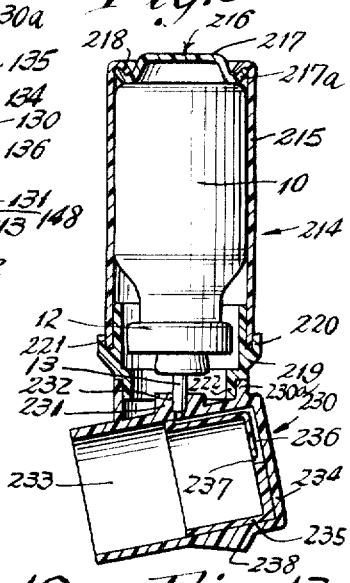
FIG. 9 shows a view of a still further form of the invention.

In the form of the invention shown in FIG. 9 the basic unit includes the bottle 10 positioned in a housing 214 having side walls 215. One end of the housing has an operating member 216 formed by a sliding closure button 217 having upturned edges 217*a* cooperating with inturned edges 218 of the adjacent side walls to prevent the button 217 from being moved out of closing position, yet permitting inward movement of the button for moving the bottle in the housing and causing the valve to be operated as will be explained. The other end of the housing is closed by a closure member 219 having a flange 220 adapted to be inserted within the walls 215 with the ends of the wall disposed in a socket 221. The wall and flange are then heat sealed to permanently secure them together The closure member has a shouldered neck 222 overlying the mounting ferrule 12 of the bottle on which the dispensing unit 230 is mounted by means of a flange 230*a* being secured thereto. The dispensing means has a central portion 231 provided with a bore 232 for receiving the stem 13 and has a transverse bore 233 having a closed end 234 forming the dispensing chamber. A thimble 235 is inserted in the bore and is provided with grooves 236 forming a passage from the valve stem to a nozzle 237 at the end of the bore adjacent the closed wall. Preferably, the dispensing chamber is set at an angle to the housing as shown in FIG. 9 so that when the end of the dispensing device is applied to the mouth in the position shown in the drawings, the container portion will be slightly tilted so as not to be interfered with by the nose while it is being operated.

In operation, the dispensing means is supported by a thumb engaging a flat bottom portion 238 in proper applying position in the mouth cavity while the finger presses on the closure button 217 to move the bottle downwardly in the housing and actuate the valve to dispense the material under pressure from the bottle.

In the form of the invention shown in FIGS. 10–13, the basic unit is the same as described above, except that it has a sliding closure member and includes the bottle 10 positioned in the plastic protective housing 14 having side walls 15. The valve mounting ferrule is secured to the neck of the bottle with the valve stem 13 projecting therefrom. The closure member 318 comprises a central projection 319, herein illustrated as cylindrical in form, having a substantially hemispherical top portion 320. The bottom end of the projection 319 is provided with a shoulder 321 connected to a flange 322 having sliding engagement with the inner surface of the walls 15. The side walls 15 have the usually lanced in tongues 21 which extend inwardly and downwardly and cooperate with the shoulder 321 to prevent the closure member from moving outwardly out of closing relationship, yet permit the closure member to move inwardly to operate the valve as will be described.

Figure 10:
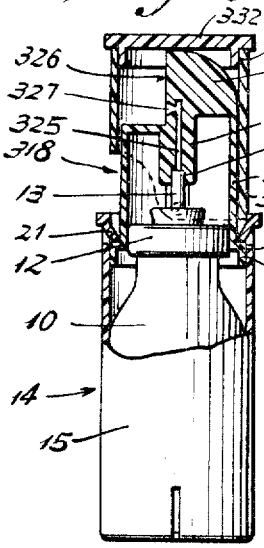
FIG. 10 shows a view, partly in section, of a still further form of the invention.
Figure 13:
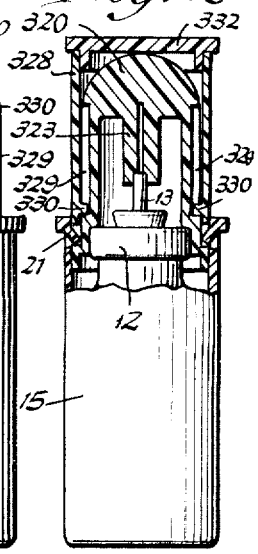
FIG. 13 is a view, partially in section, taken along lines 13—13 of FIG. 11.

The projection 319 has a central portion 323 provided with a bore 324 to receive and be secured to the end of the valve stem 13. A passage 325 extends from the bore axially of the projection and to substantially the center of the hemispherical portion as shown in FIGS. 10 and 13. The hemispherical top portion 320 of the projection is cut away, as shown in FIG. 10, to provide a laterally facing wall or surface 326 in which is positioned a suitable dispensing nozzle 327 connected to the passage 325.

Figure 11:
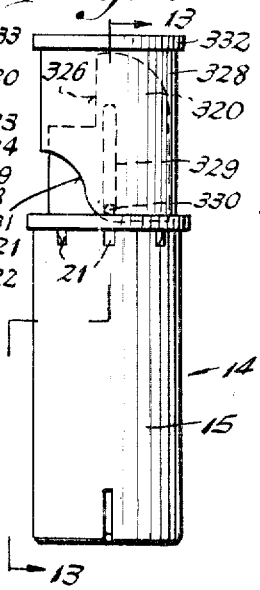
FIG. 11 is a side view of the form of the invention shown in FIG. 10.
Figure 12:
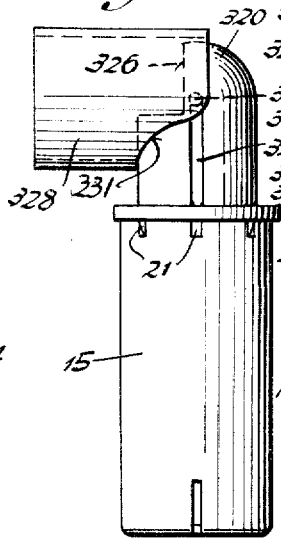
FIG. 12 is a view of the invention of FIG. 10 in a dispensing position.

Slidably mounted on the projection is a sleeve 328. As shown in FIGS. 11 to 13, the sides of the projection are provided with grooves 329 in which the integral pins 330 on the sleeve are disposed, the grooves being located in a plane which is parallel to the wall 326 having the nozzle therein and which also includes the axis of the tubular extension. The sleeve is in the normal inoperative position as shown in FIGS. 10 and 11 wherein it is in telescoping relation with the projection. However, when it is desired to use the unit to dispense the material from the package, the sleeve is raised until the pins engage the upper ends of the slots 329 and the sleeve is then pivoted into a lateral operative position as shown in FIG. 12 in which it is substantially concentric with the nozzle and forms a directing chamber for directing the passage of the aerosol material used. The side wall of the sleeve is cut away at 331, as shown in FIGS. 11 and 12, to permit the sleeve to be moved to the horizontal position and to engage and be positioned by the sides of the projecting portion 319 when in said horizontal position.

In the operative position the sleeve overlies the top of the projection so that pressure can be applied to the sleeve in the direction of the closure member causing the closure member to slide inwardly and actuate the valve to dispense material from the container.

In order to prevent inadvertent operation of the device when the sleeve is in inoperative position, it will be noted that the inner end of the sleeve in FIG. 13 engages the top of the tongues 21 and prevents inward movement of the sleeve and closure member as might cause movement of the valve to dispense material from the bottle. If desired, a plug or closure 332 having a depending flange 333 can be inserted into the end of the sleeve shown in FIGS. 10, 11 and 13 to close the end of the sleeve and prevent foreign material from passing into the sleeve to contaminate the material being dispensed therefrom.

Variations and modifications may be made within the scope of the claims and portions of the improvements may be used without others.

I claim:

1. An aerosol package comprising an unreinforced frangible bottle containing an aerosol under pressure and having a dispensing valve secured thereto provided with a projecting stem portion, a plastic protective housing of resilient shock-absorbing material having side walls and an integral end wall, the housing adapted to receive said bottle through the other open end, and a closure for said housing inserted in said open end and having a portion extending along said walls and secured thereto to prevent the closure from moving out of closing relation with the housing, said projecting valve stem extending through the closure to the outside of the housing and having a dispensing means connected thereto, said housing preventing the valve from being projected therefrom in the event of the bottle having material under pressure becoming broken.

2. An aerosol package comprising a glass bottle containing an aerosol under pressure and having a dispensing valve provided with a projecting stem portion, a plastic protective housing of resilient shock-absorbing material having side walls and an end wall, the other end of the housing being open to receive said bottle, a closure for said open end, and means including lanced-out tongue portions of said side walls adjacent the open end projecting inwardly to form abutments to interlock with the closure to prevent the closure from moving out of closing relation with the housing, said projecting valve stem having a dispensing means connected thereto.

3. An aerosol package comprising a glass bottle containing an aerosol under pressure and having a dispensing valve provided with a projecting stem portion, a plastic protective housing of resilient shock-absorbing material having side walls and an end wall, the other end of the housing being open to receive said bottle, a closure for said open end, and means including portions of said side walls adjacent the open end projecting inwardly to form abutments to interlock with the closure to prevent the closure from moving out of closing relation with the housing, said projecting valve stem projecting through said closure and having a dispensing means connected thereto, said protective housing having at least one small sight opening adjacent the end wall to permit the user to determine when the bottle is empty, said opening also venting the housing in the event of breakage of the bottle and preventing fragments of broken bottle from leaving the housing.

4. An aerosol package comprising a glass bottle containing an aerosol under pressure and having a dispensing valve provided with a projecting stem portion, a plastic protective housing of resilient shock-absorbing material having side walls and an end wall, the housing being adapted to receive said bottle through the other end, a closure for said housing inserted in the other end thereof, and means including lanced-out tongue portions of said side walls adjacent the other end of the housing projecting inwardly to form abutments to interlock with the closure to prevent the closure from moving out of closing relation with the housing, said closure having the valve stem projecting therethrough with a dispensing means connected thereto for movement therewith relative to the bottle to actuate said valve, said dispensing means having a depending flange cooperating with a neck on the closure to permit said relative movement and protect the package against foreign material.

5. An aerosol package comprising a glass bottle containing an aerosol under pressure and having a dispensing valve provided with a projecting stem portion, a plastic protective housing of resilient shock-absorbing material having side walls and an end wall, the other end of the housing being open and adapted to receive said bottle, a closure for said open end of said housing having a skirt disposed within the side walls and provided with means for centering and holding the bottle against movement therein, and means securing together the portions of said side walls and skirt to interlock and prevent the closure from moving out of closing relation with the housing, said projecting valve stem passing through the closure having a dispensing means connected thereto.

6. An aerosol package comprising a frangible unprotected glass bottle containing an aerosol under pressure and having a dispensing valve provided with a projecting tubular stem portion, a plastic shock-resistant protective housing having side walls and an end wall, the other end of the housing being open to receive said bottle, a closure for said open end having a skirt portion overlying the inner surface of the side walls adjacent the open end of the housing, and means including portions simultaneously lanced out of said side walls and skirt adjacent the open end to project inwardly and downwardly to interlock and prevent the closure from moving out of closing relation with the housing, said valve stem projecting from the open end of the housing having a dispensing means mounted thereon, said closure having means for preventing said valve from being propelled from the housing and said housing having venting means for relieving pressure therein and preventing fragments of the broken bottle from leaving the housing in the event of breakage of the bottle.

7. An aerosol package comprising a glass bottle containing an aerosol under pressure and having a dispensing valve provided with a projecting stem portion, a plastic protective housing having side walls and an end wall adapted to receive said bottle, a closure for said housing having a skirt portion overlying the inner surface of the side walls adjacent the open end of the housing, and means including portions lanced out of said side walls and skirt adjacent the open end to project inwardly and downwardly to interlock and prevent the closure from moving out of closing relation with the housing, said valve stem projecting from the housing having a dispensing means mounted thereon, the openings formed by the lanced out portions forming venting means for the housing in the event of breakage of the bottle having the aerosol under pressure, and preventing fragments of the broken bottle from leaving the housing.

8. An aerosal package comprising a glass bottle containing an aerosal under pressure and having a dispensing valve provided with a projectiing stem portion, a plastic protective housing having side walls and an end wall, the other end of the housing being open to receive said bottle, a closure for said open end having a skirt portion overlying the inner surface of the side walls adjacent the open end of the housing, and means including portions lanced out of said side walls and skirt adjacent the open end to project inwardly and downwardly to interlock and prevent the closure from moving out of closing relation with the housing, said valve stem projecting from the open end of the housing having a dispensing means mounted thereon, said housing having sight openings to permit the user to determine when the bottle is empty and also coperating with the openings formed by the lanced out portions for forming venting means for the housing in the event of breakage of the bottle having the aerosol under presure and preventing fragments of the broken bottle from leaving the housing.

9. An aerosal package comprising a glass bottle containing an aerosol under pressure and having a dispensing valve provided with a projecting tubular stem portion, a plastic protective housing having side walls and an end wall, the other end of the housing being open to receive said bottle, a closure for said open end, and means including portions of said side walls adjacent the open end projecting upwardly to form abutments to interlock with the closure to prevent the closure from moving out of closing relation with the housing, said valve stem projecting from the open end of the housing and having a dispensing means mounted thereon comprising a button having a center portion provided with a bore to receive the projecting stem portion and a passage extending to a dispensing nozzle to dispense material passing from the bottle and through the valve in response to inward movement of the stem, said button having a portion forming a cylindrical wall spaced from and concentric with the nozzle, a tubular extension slidable within the cylindrical wall from a retracted position to a projected position, means on the tubular extension and cylindrical wall portion for limiting the extension in a projected position, and a cap closing the outer end of the tubular extension.

10. An aerosol package comprising a glass bottle containing an aerosol under pressure and having a dispensing valve provided with a projecting slidable tubular stem portion, a plastic protective housing having side walls and an end wall, the other end of the housing being open to receive said bottle, a closure for said open end having a skirt portion overlying the inner surface of the side walls adjacent the open end of the housing, and means including portions lanced out of said side walls and skirt adjacent the open end to project inwardly and downwardly to interlock and prevent the closure from moving out of closing relation with the housing, said valve stem projecting from the housing having a dispensing means mounted thereon, the openings formed by the lanced out portions forming venting means for the housing in the event of breakage of the bottle having the aerosol under pressure, and preventing fragments of the broken bottle from leaving the housing, said dispensing means comprising a button having a center portion provided with a bore to receive the projecting stem portion and a lateral passage extending to a dispensing nozzle adjacent the stem to dispense material passing from the bottle and through the valve in response to inward movement of the stem, said button having a portion forming a cylindrical wall spaced from and concentric with the nozzle, a tubular extension slidable within the cylindrical wall from an inoperative retracted position to an operative projected position, means on the tubular extension and cylindrical wall portion for limiting the extension in a projected position, and a cap closing the outer end of the tubular extension, the inner end of said extension being provided with means disposed under said center portion when the extension is in inoperative retracted position to prevent inadverent inward movement of the stem to dispense the aerosol.

11. An aerosol package comprising a glass bottle containing a aerosol under pressure and having a dispensing valve provided with a tubular stem portion, a plastic protective housing having side walls and an end wall, the other end of the housing being open to receive said bottle, a closure for said open end, means securing the closure to the side walls to prevent the closure from moving out of closing relation with the housing, said valve stem projecting from the open end and having a dispensing means connected thereto and having a transverse bore closed at one end by a wall and having a center portion to receive the stem, and means disposed in the bore and having a passage means connecting the stem to a dispensing nozzle adjacent said wall.

12. An aerosol package comprising a glass bottle containing an aerosol under pressure and having a dispensing valve provided with a tubular stem portion, a plastic protective housing having side walls and an end wall, the housing being adapted to receive said bottle, a closure for said housing, and means including portions of said side walls adjacent the open end projecting inwardly to form abutment to interlock with the closure to prevent the closure from moving out of closing relation with the housing, said valve stem having a dispensing means connected thereto and having a transverse bore forming a directing chamber closed at one end by a wall, said means having a center portion to receive the valve stem and a thimble disposed in the bore and having a passage means connecting the stem to a dispensing nozzle adjacent said wall.

13. An aerosol package comprising a glass bottle containing an aerosol under pressure and having a dispensing valve provided with a tubular stem portion, a plastic protective housing having side walls and an end wall, the other end of the housing being open to receive said bottle, a closure for said open end, means including portions of said side walls adjacent the open end projecting inwardly to form abutments to interlock with the closure to prevent the closure from moving out of closing relation with the housing, said valve stem having a dispensing means connected thereto and having a transverse bore closed at one end by a wall and forming a directing chamber, said means having a center portion to receive the valve stem, and means forming an elongate passage means connecting the valve stem to a dispensing nozzle adjacent said wall, operation of said valve causing the aerosol to move along said passage and be dispensed from a point adjacent said wall into the directing chamber to be directed thereby.

14. An aerosol package comprising a glass bottle containing an aerosol under pressure and having a dispensing valve provided with a tubular stem portion, a plastic protective housing having side walls, an end wall having means to interlock with the side walls to prevent separation therefrom and slidable within the side walls to provide an operating button, the housing being adapted to receive said bottle, and a closure secured to the other end of said walls and having a dispensing means secured thereto, said valve stem being connected to said dispensing means and having a transverse bore closed at one end by a wall and having a center portion to receive the stem and a thimble disposed in the bore and cooperating therewith to form a passage means connecting the stem to a dispensing nozzle adjacent said wall to dispense material into said transverse bore upon pressure being applied to said operating button to move the bottle relative to the valve stem.

15. An aerosol package comprising a glass bottle containing an aerosol under pressure and having a dispensing valve provided with a projecting stem portion, a plastic protective housing having side walls and an end wall, the other end of the housing being open to receive said bottle, a closure for said housing having a skirt slidably mounted on said open end, and means including portions of said side walls adjacent the open end projecting inwardly to form abutments to engage a shoulder on said skirt to interlock therewith to prevent the closure from moving out of closing relation with the housing, said closure receiving the projecting valve stem and having a dispensing means thereon.

16. An aerosol package comprising a glass bottle containing an aerosol under pressure and having a dispensing valve provided with a projecting stem portion, a plastic protective housing having side walls and an end wall, the other end of the housing being open to receive said bottle, a closure for said housing having a skirt slidably mounted on said open end, and means including portions of said side walls adjacent the open end projecting inwardly to form abutments to engage a shoulder on said skirt to interlock therewith to prevent the closure from moving out of closing relation with the housing, said protective housing having at least one small sight opening adjacent the end wall to permit the user to determine when the bottle is empty, said opening also venting the housing in the event of breakage of the bottle and preventing fragments of broken bottle from leaving the housing and said closure receiving the projecting valve stem and having a dispensing means in communication therewith.

17. An aerosol package comprising a glass bottle containing an aerosol under pressure and having a dispensing valve provided with a projecting tubular stem portion, a plastic protective housing having side walls and an end wall, the other end of the housing being open to receive said bottle, a closure for said housing having a skirt slidably mounted on said open end, and means including portions of said side walls adjacent the open end projecting inwardly and downwardly to form abutments to engage a shoulder on said skirt to interlock therewith to prevent the closure from moving out of closing relation with the housing, said closure having a cylindrical projection having a central bore to receive the valve stem and terminating in a partial hemisphere having a surface parallel to the axis of the cylindrical portion provided with a laterally directed dispensing nozzle communicating with said bore, a pair of slots in the sides of the cylindrical projection extending to a point adjacent the end thereof and lying in a plane parallel to the nozzle and passing through the axis of the cylindrical portion, an extension sleeve telescoping said cylindrical portion, said sleeve having a pair of pivot pins adjacent the inner end disposed in the slots whereby said sleeve can be raised until the pivots reach the ends of the slots and the extension thereafter turned laterally to be aligned with the dispensing nozzle, the sleeve being cut away to receive the cylindrical projection when turned to said aligned position.

18. An aerosol package comprising a glass bottle containing an aerosol under pressure and having a dispensing valve provided with a projecting tubular stem portion, a plastic protective housing having side walls and an end wall, the other end of the housing being open to receive said bottle, a closure for said housing having a skirt slidably mounted on said open end, and means including portions of said side walls adjacent the open end lanced inwardly and downwardly to form abutments to engage a shoulder on said skirt to interlock therewith to prevent the closure from moving out of closing relation with the housing, said closure having a cylindrical projection having a central bore to receive the valve stem, said cylindrical projection terminating in a partial hemisphere having a surface parallel to the axis of the cylindrical portion and having a dispensing nozzle therein communicating with said bore, a telescoping extension sleeve and means mounting said sleeve for sliding and pivotal movement on said cylindrical portion whereby said sleeve can be raised and then pivoted at the end of said extension to be aligned with the dispensing nozzle.

19. An aerosol package comprising a glass bottle containing an aerosol under pressure and having a dispensing valve provided with a projecting tubular stem portion, a plastic protective housing having side walls and an end wall, the other end of the housing being open to receive said bottle, a closure for said housing having a skirt slidably mounted on said open end, and means including portions of said side walls adjacent the open end projecting inwardly and downwardly to form abutments to engage a shoulder on said skirt to interlock therewith to prevent the closure from moving out of closing relation with the housing, said closure being slidable on the housing and having a cylindrical projection provided with a central bore to receive the valve stem and to actuate the valve upon inward sliding movement, said cylindrical projection terminating in a partial hemisphere having a surface parallel to the axis of the cylindrical portion and having a dispensing nozzle therein communicating with said bore, a pair of slots in the sides of the cylindrical projection extending to a point adjacent the end thereof and lying in a plane parallel to the nozzle and passing through the axis of the cylindrical portion and an extension sleeve telescoping said cylindrical portion, said sleeve having a removable closure for the outer end and a pair of pivot pins adjacent the inner end and disposed in the slots whereby said sleeve can be raised until the pivots reach the ends of the slots and the extension thereafter turned laterally to be aligned with the dispensing nozzle, the sleeve being cut away to closely embrace the sides of the cylindrical projection when turned to said aligned position.

20. An aerosol package comprising a container having a tubular valve stem projecting therefrom and a dispensing means therefor comprising a mounting member having cylindrical projections provided with a central bore to receive the valve stem and to actuate the valve upon inward movement thereof, said cylindrical projection terminating in a partial hemisphere having a surface parallel to the axis of the cylindrical portion and having a dispensing nozzle therein communicating with said bore, a pair of slots in the sides of the cylindrical projection extending to a point adjacent the end thereof and lying in a plane parallel to the nozzle and passing through the axis of the cylindrical portion and an extension sleeve telescoping said cylindrical portion, said sleeve having a removable closure for the outer end and a pair of pivot pins adjacent the inner end and disposed in the slots whereby said sleeve can be raised until the pivots reach the ends of the slots and the extension thereafter turned laterally to be aligned with the dispensing nozzle, the sleeve being cut away to closely embrace the sides of the cylindrical projection when turned to said aligned position.

21. An aerosol package comprising a container for an aerosol under pressure having a dispensing valve provided with a tubular stem portion, and a dispensing means connected to the valve stem for movement therewith and having a transverse bore closed at one end to provide a directing chamber, said dispensing means having a center portion to receive the stem and a passage extending from the stem to a dispensing nozzle at said closed end for conducting the aerosol from the stem and projecting the aerosol into the directing chamber to travel the full length thereof to be controlled and guided thereby through the open end of the bore.

*22. In an actuator for aerosol spray dispensers which comprises an actuator sleeve member adapted to receive an aerosol can which has an outwardly projecting dis-*

*charge valve stem, the sleeve member carrying a head formed with a passageway for receiving the valve stem, a shoulder in the passageway and adapted to engage the top rim of the valve stem, and an orifice communicating with said passageway and with the exterior of said head; a cover cap member for the actuator sleeve member, the cover cap member coaxially encircling the actuator sleeve member for longitudinal sliding movement thereon, pivot means intermediate the actuator sleeve member and cover cap member and carried by one of said two members, pivot receiving and guiding means provided on the other of said members and having coaction with said pivot means, the cover cap having a cut-away wall area at its normally lower end adapting the cover cap to be swung to about horizontal dispensing position on said pivot means when, by sliding movement on the actuator sleeve, the cover cap reaches uppermost position.*

*23. The invention as defined in claim 22 wherein the end of the cover cap member in encircling position engages an abutment adapted to be carried by the aerosol can and prevents inadvertent inward movement of the actuator sleeve member.*

*24. An aerosol package comprising a container having a tubular valve stem projecting therefrom and a dispensing means therefor comprising a mounting member having cylindrical projections provided with a central bore to receive the valve stem and to actuate the valve upon inward movement thereof, said cylindrical projection terminating in a partial hemisphere and having a dispensing nozzle therein communicating said bore and the exterior of said cylindrical portion, a pair of slots in the sides of the cylindrical projection extending to a point adjacent the end thereof and lying in a plane parallel to the nozzle and passing through the axis of the cylindrical portion, and an extension sleeve telescoping said cylindrical portion, said sleeve having a pair of pivot pins adjacent the inner end and disposed in the slots whereby said sleeve can be raised until the pivots reach the ends of the slots and the extension thereafter turned laterally to be aligned with the dispensing nozzle, the sleeve being cut away to closely embrace the sides of the cylindrical projection when turned to said aligned position.*

*25. An aerosol package comprising a container having a tubular valve stem projecting therefrom and a dispensing means therefor comprising a mounting member having a cylindrical projection provided with a central bore to receive the valve stem and to actuate the valve upon inward movement thereof, said cylindrical projection terminating in a partial hemisphere and having a dispensing nozzle therein communicating said bore with the exterior thereof, a telescoping extension sleeve, and means mounting said sleeve for sliding and pivotal movement on said cylindrical portion whereby said sleeve can be raised and then pivoted at the end of said extension to be aligned with the dispensing nozzle.*

References Cited

The following references cited by the Examiner, are of record in the patented file of this patent or the original patent.

UNITED STATES PATENTS

| | | | |
|---|---|---|---|
| 1,411,542 | 4/1922 | Van Osdale | 222—156 |
| 2,948,439 | 8/1960 | Glover et al. | 222—183 |
| 2,965,100 | 12/1960 | Bridges | 222—153 X |
| 2,966,283 | 12/1960 | Darrie | 222—183 |
| 3,101,160 | 8/1963 | Picot | 222—183 |

M. HENSON WOOD, Jr., *Primary Examiner.*

ROBERT B. REEVES, *Examiner.*

N. L. STACK, *Assistant Examiner.*

UNITED STATES PATENT OFFICE

CERTIFICATE OF CORRECTION

Reissue No. 26,304 November 21, 1967

Philip Meshberg

It is hereby certified that error appears in the above numbered patent requiring correction and that the said Letters Patent should read as corrected below.

Column 2, line 30, for "the housing is formed from a strong shock resistant" read -- glass or the like frangible material, having therein --; column 7, lines 11, 12 and 31, for "aerosal" each occurrence, read -- aerosol --; line 13, for "projectiing" read -- projecting --; line 26, for "coperating" read -- cooperating --; column 8, line 15, for "a" read -- an --.

Signed and sealed this 3rd day of December 1968.

(SEAL)

Attest:

Edward M. Fletcher, Jr.
Attesting Officer

EDWARD J. BRENNER
Commissioner of Patents